United States Patent [19]

Teed

[11] 4,089,728
[45] May 16, 1978

[54] WORKPIECE MONITORING AND CONTROL APPARATUS FOR A MACHINE HAVING A SEQUENTIAL FLOW OF WORKPIECES

[75] Inventor: Richard K. Teed, Greenwood, S.C.

[73] Assignee: Riegel Textile Corporation, New York, N.Y.

[21] Appl. No.: 687,000

[22] Filed: May 17, 1976

[51] Int. Cl.² .............................................. B65C 9/40
[52] U.S. Cl. .................................................. 156/352
[58] Field of Search ............................... 156/350–352, 156/361–367, 64, 378; 340/259

[56] References Cited

U.S. PATENT DOCUMENTS

| 3,339,195 | 8/1967 | Murlet | 340/259 |
| 3,553,041 | 1/1971 | Von Hofe | 156/378 |
| 3,981,763 | 9/1976 | Brocklehurst | 156/352 |

*Primary Examiner*—David A. Simmons
*Attorney, Agent, or Firm*—Bell, Seltzer, Park & Gibson

[57] ABSTRACT

Workpiece monitoring and control apparatus for a machine having a desired predetermined sequential flow of equally spaced-apart workpieces therein and being characterized by continually monitoring both the presence and absence of workpieces in such flow and operating control mechanisms for such machine, such as stopping operation of the machine or actuating a signalling device, in the event of an undesired absence or presence of a workpiece. The monitoring and control apparatus includes an electrically operated machine control device, sensing devices positioned in the sequential flow of the equally spaced-apart workpieces for sensing the passage of workpieces and for sensing the absence of workpieces in such flow and an electrical circuit connected with the control devices and with the sensing devices for normally supplying electrical energy to the control devices and being responsive to the sensing devices for stopping the supply of electrical energy to the control devices when the sensing devices (1) fail to sense a workpiece in each desired equally spaced-apart position in the sequential flow or (2) fails to sense the absence of a workpiece between such desired position.

12 Claims, 6 Drawing Figures

WORKPIECE MONITORING AND CONTROL APPARATUS FOR A MACHINE HAVING A SEQUENTIAL FLOW OF WORKPIECES

This invention relates to workpiece monitoring and control apparatus for a machine having a desired predetermined sequential flow of equally spaced-apart workpieces therein and being characterized by continually monitoring both the presence and the absence of workpieces in such flow and operating control mechanisms for such machine, such as stopping operation of the machine or actuating a signalling device, in the event of an undesired absence or presence of a workpiece. Specifically, the invention relates to such workpiece monitoring and control apparatus for use in a machine for the manufacture of articles having tabs, labels or strips applied thereto and, more specifically, to an apparatus for the manufacture of disposable diapers having fastener tabs applied on each longitudinal edge thereof at equally spaced-apart locations on a continuous web being manufactured into such disposable diapers.

BACKGROUND OF THE INVENTION

Various article fabricating machines and other machines utilize a desired predetermined sequential flow of equally spaced-apart workpieces therethrough during the fabricating or other operations by the machine. Devices have been proposed for such machines for monitoring this desired sequential flow of workpieces and operating control mechanisms for such machines in the event of the absence of a workpiece in the desired position of such sequential flow such as shown in application Ser. No. 549,049, filed Feb. 11, 1975, now U.S. Pat. No. 3,981,763, issued Sept. 21, 1976, and assigned to the assignee of the present invention. Such devices have for the most part included photoelectric cell mechanisms for sensing the passage of workpieces in the desired sequential flow.

The above types of machines include, inter alia, machines for fabricating individual articles in which it is desired to monitor the articles, machines for applying tabs, labels or strips to a continuous web of material during fabrication of articles from such web in which it is desired to monitor the tabs, labels or strips, and more specifically disposable diaper fabricating machines in which fastener tabs are applied at predetermined equally spaced-apart locations on each longitudinal edge of a continuous web of material being manufactured into such diapers in which it is desired to monitor the tabs applied to each longitudinal edge, such as shown in copending application Ser. No. 491,739, filed July 25, 1974, now U.S. Pat. No. 3,984,272, issued Oct. 5, 1976, and assigned to the assignee of the present invention.

The devices heretofore utilized with such machines for monitoring the predetermined spaced-apart sequential flow of workpieces or tabs, labels or strips were constructed for sensing the presence of such workpiece, tab, strip or label at the desired locations in the sequential flow for operating control mechanisms, such as stop devices or signalling devices in the event the sensing devices failed to sense such workpiece or tab, label or strip at each such location; however, were not constructed to sense the absence of workpieces, tabs, strips or labels between the desired locations in the sequential flow. Consequently, the sensing devices often malfunctioned and operated as though a workpiece, tab, strip or label was continuously present. Therefore, if such workpiece, tab, strip or label was absent of the desired locations or was improperly positioned between desired locations, the sensing mechanisms would fail to recognize this and the machine operation would continue with the improper positioning present.

This was particularly prevalent with photoelectric cell sensing devices in which the sensitivity thereof could be either improperly adjusted or be malfunctioning so that the photoelectric cell sensing means though it was sensing a workpiece, tab, strip or label continuously during the flow through such machines and failed to properly monitor and actuate the control mechanisms of the machine. Also, the reverse often occurred where the sensing device could malfunction to continually sense the absence of a workpiece, tab, strip or label.

OBJECTS AND SUMMARY OF THE INVENTION

Accordingly, it is the object of this invention to overcome the problems provided by prior workpiece monitoring and control apparatus for machines having a desired predetermined sequential flow of equally spaced-apart workpieces therein by providing workpiece monitoring and control apparatus which continually monitors both the presence and absence of workpieces in such flow and operates control mechanisms for the machine in the event of the sensing of either an undesired absence or presence of a workpiece.

It has been found by this invention that the above object may be accomplished by providing such monitoring and control apparatus which comprises electrically operated control means, sensing means positioned in the sequential flow of the equally spaced-apart workpieces for sensing the passage of workpieces and for sensing the absence of workpieces in such flow, and electrical circuit means connected with the control means and with the sensing means for normally supplying electrical energy to the control means and being responsive to the sensing means for stopping the supply of electrical energy to the control means when the sensing means (1) fails to sense a workpiece in each desired equally spaced-apart position in the sequential flow or (2) fails to sense the absence of a workpiece between such desired positions.

The present invention also provides such monitoring and control apparatus for specific use with an apparatus for the manufacture of articles having tabs, labels or strips applied at predetermined, equally spaced-apart locations on material being manufactured into articles by apparatus and, more specifically, to a disposable diaper fabricating machine in which fastener tabs are applied on each longitudinal edge of a continuous web of material being fabricated into such articles.

In the case of a disposable diaper machine, a first sensing means is positioned adjacent the fastener tab means on one side of the path of travel of the material for sensing the presence of the fastener tabs applied onto one side of the moving material at the desired locations and for sensing the absence of fastener tabs between the desired locations on the one side of the moving material. Second sensing means are positioned on the other side of the moving material at the same location and for the same purpose as the first sensing means for monitoring the fastener tabs on the other longitudinal edge of the material. The electrical circuit means is responsive to both the first and second sensing means in the manner described above.

Preferably, the sensing means of this invention comprises a photoelectric means including light emitting lamp means and photocell receiver means, and the electrical circuit includes timer switch means, which may be in the form of first and second cam operated limit switches, cooperating with the photoelectric means for interrupting the supply of electrical energy to the control means when the photoelectric means fails to sense a workpiece in each desired position or fails to sense the absence of a workpiece between such desired positions.

Preferably, a relay operated switch means is provided in the electrical circuit including a relay connected with and being responsive to the sensing means, a first switch connected in the circuit and parallel with the first timer operated switch for being closed by the relay in response to the sensing of a workpiece in the desired position in the sequential flow by the sensing means for maintaining the flow of electrical energy thereto and to the control means for the timed periods during which the first timer operated switch momentarily opens, and a second switch connected in the circuit in parallel with the second timer operated switch for being closed by the relay in response to the sensing of the absence of a workpiece between the desired positions in the sequential flow by the sensing means for maintaining the flow of electrical energy therethrough and to the control means for the timed periods during which the second timer operated switch momentarily opens.

Accordingly, in the event of an undesired absence or an undesired presence of a workpiece in the sequential flow, either the first or second relay operated switches will not be closed during respective openings of the first or second timer operated switches to stop the flow of electrical energy to the control means.

BRIEF DESCRIPTION OF THE DRAWINGS

Some of the objects and advantages of the invention having been stated, others will appear as the description proceeds when taken in conjunction with the accompanying drawings, in which —

DESCRIPTION OF PREFERRED EMBODIMENT

Figure 1:
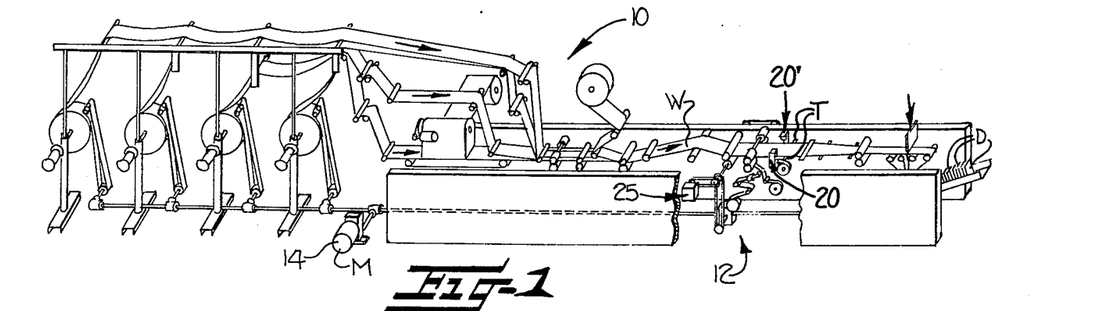
FIG. 1 is a schematic perspective view of an apparatus for the manufacture of disposable diapers having mechanisms thereon for applying fastener tabs to each longitudinal edge of the web of material being manufactured into such diapers and utilizing the workpiece monitoring and control apparatus of this invention.
Figure 2:
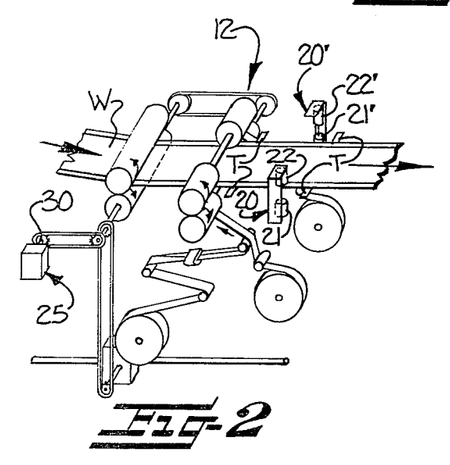
FIG. 2 is an enlarged perspective view of the portion of the apparatus of FIG. 1 for applying fastener tabs to each longitudinal edge of a continuous web of material being manufactured into disposable diapers and illustrating photoelectric sensing means forming a part of the monitoring and control apparatus of this invention.
Figure 6:
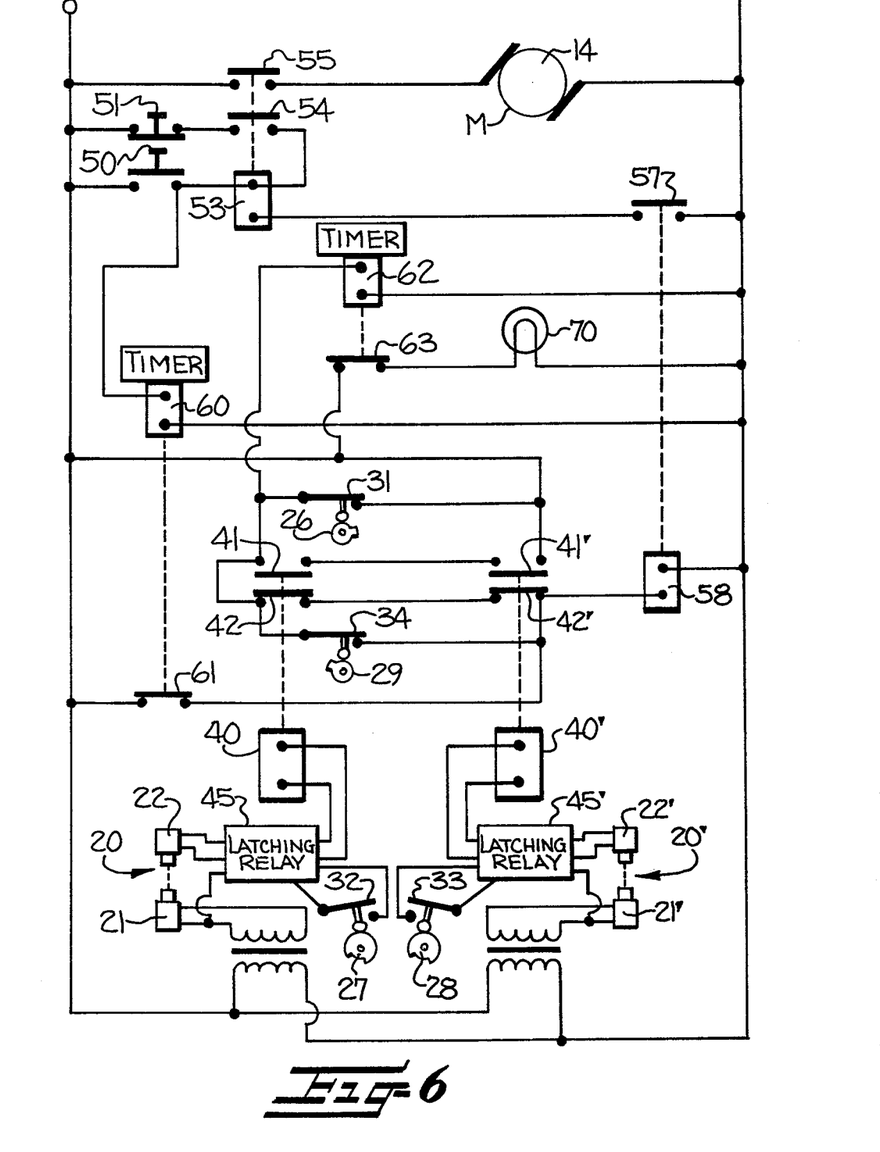
FIG. 6 is an electrical schematic view of the preferred form of the monitoring and control apparatus of this invention as may be utilized for the disposable diaper fabricating machine of FIG. 1.

Referring now to the drawings, a preferred form of workpiece monitoring and control apparatus is illustrated therein, particularly in FIG. 6, for use with a disposable diaper fabricating machine, as shown in FIG. 1 and generally indicated at 10, including mechanisms 12, shown in FIGS. 1 and 2, for applying equally spaced-apart fastener tabs T to each longitudinal edge of a formed continuous web of material W being manufactured into disposable diapers D. Details of the construction and operation of the disposable diaper fabricating machine 10 and the fastener tab applying mechanisms 12 may be seen in the aforementioned assignee's prior copending U.S. patent applications Ser. Nos. 491,793 and 549,049 now U.S. Pat. Nos. 3,984,272 and 3,981,763. However, it is to be understood that the workpiece monitoring and control apparatus of this invention would have utility in other types of article fabricating machine and other types of machines in which a desired predetermined sequential flow of equally spaced-apart workpieces is present and wherein it is desired to operate control mechanisms, such as machine stop devices or signalling devices, in the event of an undesired absence or presence of a workpiece in such flow through the machine.

As shown in FIG. 1 and in the above referred to prior applications of the assignee of the present invention, the disposable diaper fabricating machine 10 forms individual disposable diapers D from a multi-layered, diaper-forming web W which is formed from several layers of sheet material fed through the machine 10 in the direction of the arrows indicated in FIG. 1. The diaper fabricating machine 10 is operated and driven by a control means or drive motor 14. As the continuous web of diaper forming material W travels through the machine 10, it passes the mechanisms 12 for applying the spaced-apart fastener tabs T to each longitudinal edge of the web W. The fastener tab applying mechanisms 12 are also suitably driven from the main machine drive motor 14, as indicated schematically in FIGS. 1 and 2.

From the standpoint of economy and high production, it is desirable to operate the diaper forming machine 10 at as high a rate of production as is practical. Therefore, it is important that a tab T is applied at each desired, equally spaced-apart, location along each longitudinal edge of the continuous web W of material being fabricated into such diapers D. If such tabs T are not applied by the mechanisms 12 at each desired location on each side of the web W or are applied at undesired locations between desired locations on either side of the web W, it is desired to stop operation of both the machine 10 and mechanisms 12 for repair to obviate the need for expending extra time and labor for inspecting and applying any missing fastener tabs or removing any mispositioned fastener tabs from the fabricated diapers D after they have been discharged from the machine 10.

Accordingly, monitoring and control apparatus, as shown schematically in FIG. 6, is provided for the disposable diaper fabricating machine 10 for continually monitoring both the presence and the absence of fastener tabs T at the desired locations on each side of the moving web of material W and for stopping operation of the drive motor 14 controlling operating of both the machine 10 and the mechanisms 12 in the event of an undesired absence or presence of such fastener tabs T.

The monitoring and control apparatus includes a first sensing means 20, preferably a photoelectric device including a light emitting lamp 21 and a photocell receiver 22, positioned adjacent the fastener tab applying mechanisms 12 and downstream of the path of travel of the web W on one longitudinal edge thereof for sensing the presence of fastener tabs T applied onto the one side of the moving web of material W at the desired equally spaced-apart locations in the sequential flow and for sensing the absence of fastener tabs T between the desired locations on the one side of the moving material.

Likewise, an identical second sensing means 20', preferably a photoelectric device including a light emitting lamp 21' and a photocell receiver 22', is positioned adjacent the fastener tab applying mechanisms 12 and downstream of the path of travel of the web of material W therefrom on the other longitudinal edge thereof for sensing the presence of the fastener tabs T applied on the other side of the moving web of material W at the spaced-apart desired locations for sensing the presence of fastener tabs T and the absence of the fastener tabs T between the desired locations on the other side of the moving web of material W.

The monitoring and control apparatus of this invention further includes an electrical circuit means, as shown in FIG. 6, having an electrical circuit with a source of electrical energy and connected with the machine drive motor 14 and both the first and second sensing means 20, 20' for normally supplying electrical energy to the drive means 14 for operation thereof and being independently responsive to either or both of the first and second sensing means 20, 20' to stop the supply of electrical energy to the drive means 14 for stopping operation of the machine 10 and the tab applying mechanisms 12 when either or both of said first and second sensing means 20, 20' (1) fails to sense a tab at the desired positions on the moving material or (2) fails to sense the absence of a fastener tab between such desired positions on the moving material.

Figure 3:
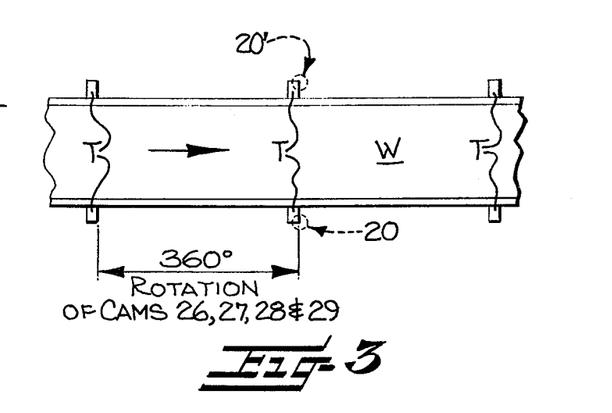
FIG. 3 is a schematic, top plan view of the web of material which is manufactured into disposable diapers by the apparatus of FIG. 1 and illustrating the positioning of the photoelectric cell sensing means and the desired positioning of the fastener tabs on such web of material.
Figure 4:
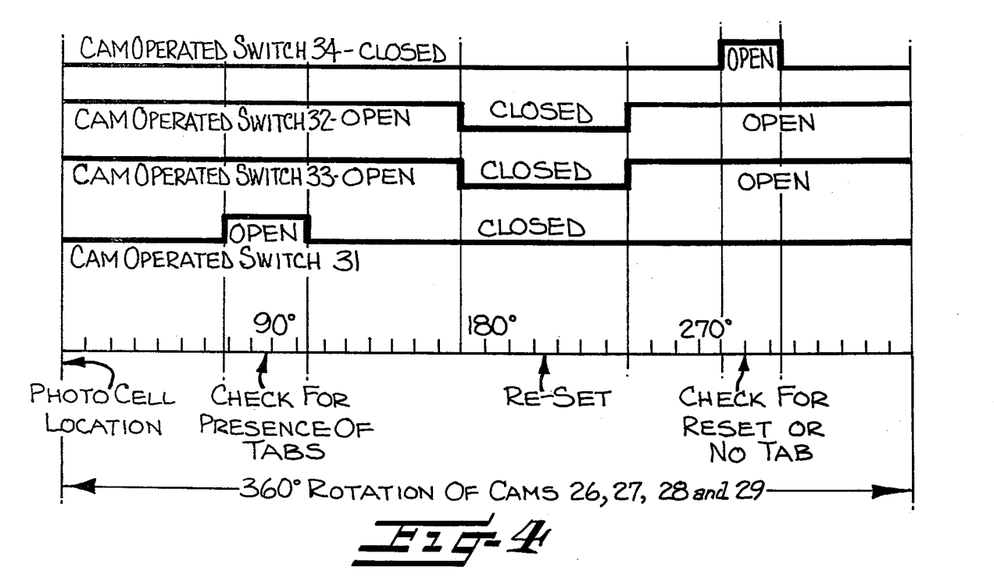
FIG. 4 is a schematic chart illustrating the opening and closing of the cam operated timer switches in relation to 360° of rotation of the timer cams for the four timer operated switch devices utilized in a preferred form of the monitoring and control apparatus of this invention.
Figure 5:
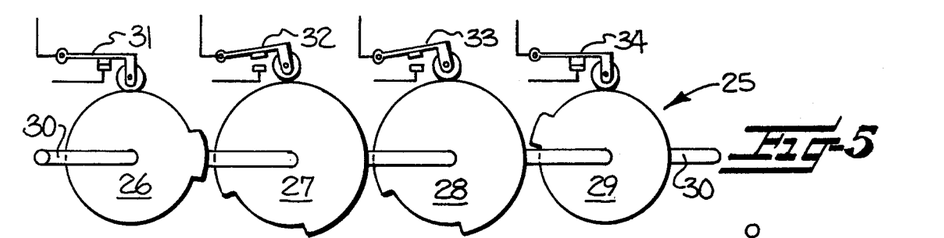
FIG. 5 is a perspective, side elevational view of the cam operated timer switches utilized in a preferred form of the monitoring and control apparatus of this invention.

The electrical circuit means includes timer switch means, generally indicated at 25 in FIG. 5, preferably in the form of cam operated limit switches, cooperating with the sensing means 20, 20' for interrupting the supply of electrical energy through the electrical circuit to the control or drive means 14 when the sensing means 20, 20' either fails to sense a tab T in each desired position or fails to sense the absence of a tab T between such desired positions. The timer switch means 25 is a commercially available mechanism in which a desired number of cams 26, 27, 28 and 29 are commonly mounted on a driven shaft 30 and may be desirably profiled to open or close corresponding limit switches 31, 32, 33 and 34, as desired. When utilized with the machine 10 and the mechanisms 12, each of the cams 26–29 are timed to rotate 360° during the period of time necessary for each spaced-apart tab T to pass the sensing means 20, 20', as indicated schematically in FIG. 3. The respective camming operations for opening and closing of the switches 31–34 during such 360° cycle of rotation is indicated schematically in FIG. 4, for purposes to be described below.

As may be seen in FIG. 6, the electrical circuit means includes a first timer operated switch means in the circuit comprising normally closed switch 31 operated by the cam 26 for maintaining the flow of electrical energy, when closed, through the circuit and to the drive motor 14. As may be seen in FIGS. 4, 5 and 6, the cam 26 operates for momentarily opening the switch 31 during a predetermined time period in its 360° cycle of rotation and during which time the sensing means 20, 20', should be sensing a tab T.

A second timer operated switch means is connected in the circuit and comprises normally closed switch 34 connected in series with the first timer operated switch 31 for maintaining the flow of electrical energy through the circuit and to the drive motor 14, and cam 29 for momentarily opening the switch 34 during a predetermined time period of its 360° cycle of rotation and during which time the sensing means 20, 20' should be sensing the absence of a tab T.

The electrical circuit means further includes first and second relay operated switch means including electromagnetic relays 40, 40' connected with and being responsive to the respective photoelectric cell sensing means 20, 20', normally open switches 41, 41' connected in the circuit in parallel with the first timer operated switch 31 for being closed by the respective relays 40, 40' in response to the sensing of a fastener tab on the moving material by the photoelectric cell sensing means 20, 20' for maintaining the flow of electrical energy through the circuit and to the drive motor 14 for the timed periods during which the switch 31 is opened by the cam 26, and normally closed switches 42, 42' connected in the circuit in parallel with the second timer operated switch 34 for being closed by the relays 40, 40' in response to the sensing of the absence of a fastener tab between the desired positions on the moving web W by the photoelectric cell sensing means 20, 20' for maintaining the flow of electrical energy through the circuit and to the drive motor 14 for the timed periods during which the cam 29 of the second timer operated switch momentarily opens the switch 34.

The photoelectric sensing means 20, 20' are both of a type in which the light emitting lamps 21, 21' normally direct respective beams of light across the paths of the respective fastener tabs T projecting laterally from opposite side edges of the web W. These light beams are focused to impinge on the photocell receivers 22, 22' which are of a type that conduct electricity or are active in the absence of a light of predetermined intensity impinging thereon so that the photocell receivers 22, 22' are rendered active upon interruption of the light beams by a corresponding tab T.

Interposed between the respective photoelectric cell sensing means 20, 20' and the respective first and second relay operated switch means are first and second latching relays 45, 45'. The latching relays 45, 45' are of a well known commercial type which are activated and remain activated upon receiving electrical energy occurring when the respective photoelectric cell sensing means 20, 20' senses the presence of a fastener tab T in the desired position on the respective sides of the moving web of material W. When the respective latching relays 45, 45' are activated, they in turn activate the respective electromagnetic relays 40, 40' for closing the normally open switches 41, 41' and opening normally closed switches 42, 42'.

Associated with each of the respective latching relays 45, 45' are the third and fourth cam operated timer switches 32, 33 which are operated by the respective cams 27, 28 to close the normally open switches 32, 33 during the portion of the 360° cycle of rotation thereof during which the absence of a fastener tab T is intended to be sensed by the respective photocell sensing means 20, 20'. When the respective switches 32, 33 are closed by the cams 27, 28, the respective latching relays 45, 45' will be deactivated which in turn deactivates the electromagnetic relays 40, 40' allowing the switches 41, 42 and 41', 42' to return to their normal positions.

Accordingly, in operation of the monitoring and control means of this invention, each time a pair of properly positioned tabs T interrupt the respective light beams of the photoelectric cell sensing devices 20, 20', the photoelectric cell sensing devices will be rendered momentarily conductive to activate the respective latching relays 45, 45', which in turn energize the respective electromagnetic relays 40, 40' to move the normally open switches 41, 41' to their closed positions and to move the normally closed switches 42, 42' to their open positions.

At the instant the relays 40, 40' are activated and the switches 41, 41' are closed by the respective fastener tabs T moving into the paths of the photoelectric cell sensing devices 20, 20', the timer operaed switch 31 is closed and is completing a circuit to the drive motor 14. However, thereafter and during the interval in which the relays 40, 40' are still supposed to be active holding the switches 41, 41' closed, the cam 26 momentarily engages and opens the first timer operated switch 31. In this event, should both the relays 40, 40' not be active when the switch 31 opens, the circuit to the drive motor 14 is interrupted and operation of the machine 10 and mechanisms 12 stop.

After the first timer operated switch 31 has returned to its closed position, normally open timer operated switches 32, 33 are closed by the respective cams 27, 28. This resets the latching relays 45, 45' interrupting power to the electromagnetic relays 40, 40' causing switches 42, 42' to close and switches 41, 41' to open. After the switches 42, 42' have returned to their normally closed position, the normally closed timer switch 34 is momentarily opened by cam 29. Should both latching relays 45, 45' not be reset and thus relays 40, 40' be in the inactive state closing switches 42, 42' when the switch 34 opens, the circuit to the drive motor 14 is interrupted and operation of the machine 10 and mechanisms 12 stops.

It may thus be seen that, upon failure of either or both of the photoelectric sensing devices 20, 20' to properly sense the presence and the absence of tabs T on the corresponding length of web W, the respective latching relays 45, 45' wil not be cycled and, consequently, the respective electromagnetic relays 40, 40' will not be cycled. Therefore, when the cam 26 operates to momentarily open the first timer operated switch 31, since the circuit cannot be completed through the open switches 41, 41' of the respective relays 40, 40' to the drive motor 14, it is apparent that the first timer operated switch 31 will interrupt the circuit to the drive motor 14.

It may also be seen that on the deactivation cycle that should latching relays 45, 45' fail to reset by the action of timer operated switches 32, 33 being closed by cams 27, 28 or should the photocell sensing devices 20, 20' falsely operate as if it senses a fastener tab T after the cams 27, 28 have closed the switches 32, 33, resetting of the latching relays 45, 45' is not accomplished and the relays 40, 40' do not return the switches 41, 41', 42, 42' to their normal position so that when cam 29 momentarily opens the second timer operated switch 34, the circuit to the drive motor 14 will be interrupted stopping operation of the machine 10 and the mechanisms 12.

The electrical circuit means further includes a normally open, manually operable, push-button, "start" switch 50, a manually operable, normally closed, push-botton "stop" switch 51, and an electromagnetic motor starter and holding relay 53 provided with normally open switches 54, 55. The electrical circuit means further includes a normally open switch 57 of a motor stop motion relay 58. The switch 57 is arranged in series with the coil of the holding relay 53 so that the coil of the stop motion relay 58 must be energized for closing of the switch 57 in order for the motor 14 to be energized. Operation of the stop motion relay 58 which is connected in series with the relay switches 41 41', 42, 42' and timer operated switches 31, 34 is also controlled by the sensing devices 20, 20'.

It is also desirable to provide a visual or audible warning signal, adjacent the fastener tab applying mechanisms 12, which will be activated each time the absence of a tab T on the web W causes stoppage of the motor 14. Further, it is desirable to reset the circuit by automatically energizing the coil of stop motion relay 58 immediately following the de-energizing of the motor 14 effected by the opening of the switch 57 by the stop motion relay 58. Otherwise, the subsequent manual closing of "start" switch 50 would not affect operation of the motor 14, as would be necessary in order to correct the malfunction of the machine 10 or to resume normal operation of the machine 10.

Accordingly, the electrical circuit means further includes electromagnetically operable timer relays or time-delay relays 60, 62 which are provided with respective normally closed switches 61, 63 which are closed immediately upon de-energizing of the coils of the respective timer relays 60, 62 and which then remain closed until the timer coils of the relay 60, 62 are re-energized and for a time period after re-energizing occurs. The switch 61 of the time delay relay 60 is normally closed, but is held open during normal operation of the machine 10 and motor 14. The coil of the timer delay relay 60 is arranged in parallel with the coil of the holding relay 53 and thus is energized and de-energized by the respective closing and opening of the switch 57 of the stop motion relay 58, stop switch 50, start switch 51 and switch 54 of holding relay 53. When the coil of relay 60 is de-energized, the closing of its switch 61 bypasses the photocell sensing systems and activates coil 58 of the stop motion relay causing switch 57 to close and allowing the motor 14 to be started. Starting of the motor 14 by activating start switch 51 activates relay 53 and activates the timer of relay 60. After a predetermined time, relay 60 is activated opening switch 61 removing the bypass of the photoelectric cell sensing system.

The switch 63 of time delay relay 62 is normally closed but is held open during normal operation of the motor 14 and the machine 10. The coil of time delay relay 62 is in series with switches 41, 41' and also timer operated switch 31. An open circuit to the time delay relay 62 occurs when either or both of the tabs are missing and either or both of the switches 41, 41' are open when timer cam 26 opens switch 31. The open circuit to relay 62 causes switch 63 to return to its normally closed position activating an electrically operable warning device or lamp 70. The lamp 70 will remain on until power is restored to the relay 62 and for a predetermined period of time thereafter so as to insure that an operator may be alerted by the warning device 70 to take any corrective measures which may be required.

From the foregoing description, it is clear that the main drive motor 14 is initially energized by the momentary manual closing of start switch 50, which effects energization of the coil of motor starter and holding relay 53 through the then closed switch 57. The switches 54, 55 of the starter relay 53 then move to closed position and the flow of electricity through the coil of starter relay 53 is maintained through the start switch 50 and switch 54 as the switch 55 establishes the circuit to drive motor 14.

Thus it may be seen, that the control and monitoring apparatus of this invention provides a mechanism which cannot be misadjusted or malfunction and which must sense both the presence of fastener tabs T at the equally spaced-apart desired predetermined locations on each side of a web of material W and must sense the absence of such fastener tabs between desired positions for maintaining an electrical circuit to the drive motor 14 of the diaper fabricating machine 10 and the tab applying mechanisms 12.

It will be readily apparent that the monitoring and control apparatus of this invention may also be utilized for the sensing of single strips, tabs or labels or the sensing of individual workpieces in any desired machine and for controlling operation of control mechanisms or a drive motor. In the event that single workpieces are to be monitored instead of pairs of workpieces, the mechanisms described and illustrated in FIG. 6 could be easily modified to eliminate the devices indicated therein with prime notations and the corresponding timer operated switch 33 controlled by cam 28.

In the drawings and specifications there has been set forth a preferred embodiment of the invention, and although specific terms are employed, they are used in a generic and descriptive sense only and not for purposes of limitation.

What is claimed is:

1. Workpiece monitoring and control apparatus for a machine having a desired predetermined sequential flow of equally spaced-apart workpieces therein and being characterized by continually monitoring both the presence and absence of workpieces in such flow and operating control mechanisms for such machine, such as stopping operation of the machine or actuating a signaling device, in the event of an undesired absence or presence of a workpiece; said monitoring and control apparatus comprising:

electrically-operated machine control means;

sensing means positioned in the sequential flow of the equally spaced-apart workpieces for sensing the passage of workpieces and for sensing the absence of workpieces in such flow;

a source of electrical energy;

an electrical circuit connected between said source of electrical energy and said electrically-operated control means for effecting the flow of electrical energy therebetween and connected with said sensing means;

first timer-operated switch means in said circuit comprising a normally closed switch for maintaining the flow of electrical energy therethrough and to said control means, and timer means for momentarily opening said switch during first predetermined timed periods;

second timer-operated switch means in said circuit comprising a normally closed switch connected in series with said first timer-operated switch means for maintaining the flow of electrical energy therethrough and to said control means, and timer means for momentarily opening said second switch during second predetermined timed periods different from the first timed periods; and relay-operated switch means including a relay connected with and being responsive to said sensing means, a first switch connected in said circuit in parallel with said first timer-operated switch for being closed by said relay in response to the sensing of a workpiece in the desired position in the sequential flow by said sensing means for maintaining the flow of electrical energy therethrough and to said control means for the timed periods during which said first timer means momentarily opens said first timer-operated switch, and a second switch connected in said circuit in parallel with said second timer-operated switch for being closed by said relay in response to sensing of the absence of a workpiece between the desired positions in the sequential flow by said sensing means for maintaining the flow of electrical energy therethrough and to said control means for the timed periods during which said second timer means momentarily opens said second timer-operated switch;

whereby, in the event of an undesired absence or undesired presence of a workpiece in the sequential flow, either said first or second relay-operated switches will not be closed during the respective opening of said first and second timer-operated switch means to stop the flow of electrical energy to said control means.

2. Workpiece monitoring and control apparatus, as set forth in claim 1, in which said sensing means comprises photoelectric means including light emitting lamp means and photocell receiver means.

3. Workpiece monitoring and control apparatus, as set forth in claim 1, in which said timer operated switch means comprises cam operated limit switch means.

4. Workpiece monitoring and control apparatus, as set forth in claim 1, in which said electrically operated machine control means comprises an electrically operated drive motor for the machine.

5. Workpiece monitoring and control apparatus, as set forth in claim 1, in which said first relay operated switch comprises a normally open switch which is closed by said relay upon actuation thereof, and said second relay operated switch comprises a normally closed switch which is opened by said relay upon actuation thereof.

6. Workpiece monitoring and control apparatus, as set forth in claim 5, in which said electrical circuit means further includes latching relay means connected with said sensing means for being activated thereby when said sensing means senses the presence of a workpiece in the desired position in the flow and connected with said relay of said relay operated switch means for actuation thereof when activated by said sensing means, and third timer operated switch means connected with said latching relay means for deactivating said latching relay means and thus deactuating said relay of said relay operated switch means during predetermined timed periods in which the absence of a workpiece is desired to be sensed by said sensing means.

7. Workpiece monitoring and control apparatus, as set forth in claim 6, in which said sensing means comprises photoelectric means including a light emitting lamp and a photocell receiver positioned for the flow of workpieces therebetween, said photocell receiver being connected with said latching relay means for activation thereof when a workpiece passes between said lamp and photocell receiver.

8. Workpiece monitoring and control apparatus, as set forth in claim 1, in which said electrical circuit means further includes manually operated normally open start switch means in said circuit for being momentarily closed to initiate the flow of electrical energy to said control means, manually operated normally closed stop switch means in said circuit for being opened to stop the flow of electrical energy to said control means, relay operated normally open holding switch means connected in said circuit in series with said start switch means and said stop switch means for being closed by said start switch when said start switch means is momentarily closed for maintaining the flow of electrical energy to said control means and for being held closed by said stop switch means until said stop switch means is opened, relay operated stop motion switch means comprising a relay connected in series with said first and second timer operated switch means and said sensing means responsive, relay operated switch means for being activated and deactivated thereby, and a normally open switch connected in said circuit in series with said relay operated holding switch means for being closed upon activation of said stop motion relay for maintaining said holding switch means closed and for being opened upon deactivation of said stop motion relay for opening said holding switch means to stop the flow of electrical energy to said control means, and timer operated reset switch means connected in said circuit in series with said stop motion relay for closing of said normally open stop motion switch after said stop motion switch has been opened to stop the flow of electrical energy to said control means for allowing restarting by said start switch means.

9. In an apparatus for the manufacture of disposable diapers having fastener tabs on each longitudinal edge thereof and including means for continuously moving material being manufactured into such diapers through said apparatus, means for applying such fastener tabs at predetermined equally spaced-apart locations to each side of the moving material, and electrically-operated drive means operatively connected with said material moving means and said tab applying means for driving both of said means; the combination therewith of monitoring and control apparatus for continually monitoring both the presence and absence of fastener tabs at the desired locations on each side of the moving material and for stopping operation of said drive means in the event of an undesired absence or presence of such fastener tabs, said monitoring and control apparatus comprising:

first sensing means positioned adjacent said fastener tab applying means on one side of the path of travel of the material therefrom for sensing the presence of the fastener tabs applied onto the one side of the moving material at the desired location and for sensing the absence of fastener tabs between the desired locations on the one side of the moving material;

second sensing means positioned adjacent said fastener tab applying means on the other side of the material for sensing the presence of the fastener tabs applied on the other side of the moving material at the desired locations and for sensing the absence of the fastener tabs between the desired locations on the other side of the moving material;

a source of electrical energy;

an electrical circuit connected between said source of electrical energy and said electrically-operated drive means for effecting the flow of electrical energy therebetween and connected with each of said sensing means;

first timer-operated switch means in said circuit comprising a normally closed switch for maintaining the flow of electrical energy therethrough and to said drive means, and cam-operated timer means for momentarily opening said switch during first predetermined timed periods;

second timer-operated switch means in said circuit comprising a normally closed switch connected in series with said first timer-operated switch for maintaining the flow of electrical energy therethrough and to said drive means, and cam-operated timer means for momentarily opening said second switch during second predetermined timed periods different from the first timed periods;

first relay-operated switch means including a relay connected with and being responsive to said first sensing means, a normally opened switch connected in said circuit in parallel with said first timer-operated switch for being closed by said relay in response to the sensing of a fastener tab on the moving material by said first sensing means for maintaining the flow of electrical energy therethrough and to said drive means for the timed periods during which said first timer means momentarily opens said first timer-operated switch, and a normally closed switch connected in said circuit in parallel with said second timer-operated switch for being closed by said relay in response to the sensing of the absence of a fastener tab between the desired positions on the moving web by said first sensing means for maintaining the flow of electrical energy therethrough and to said drive means for the timed periods during which said second timer means momentarily opens said second timer-operated switch; and second relay-operated switch means including a relay connected with and being responsive to said second sensing means, a normally opened switch connected in said circuit in parallel with said first timer-operated switch for being closed by said relay in response to the sensing of a fastener tab on the moving material by said second sensing means for maintaining the flow of electrical energy therethrough and to said drive means for the timed periods during which said first timer means momentarily opens said first timer-operated switch, and a normally closed switch connected in said circuit in parallel with said second timer-operated switch for being closed by said relay in response to the sensing of the absence of a fastener tab between the desired positions on the moving web by said second sensing means for maintaining the flow of electrical energy therethrough and to said drive means for the timed periods during which said second timer means momentarily opens said second timer-operated switch;

whereby, in the event of an undesired absence or an undesired presence of a fastener tab on either side of the moving web, either said first or second relay-operated switches will not be closed during the respective openings of said first and second timer-operated switch means to stop the flow of electrical energy to said drive means.

10. Apparatus, as set forth in claim 9, in which
each of said sensing means comprises photoelectric means including light-emitting lamp means and photocell receiver means.

11. Apparatus, as set forth in claim 10, in which said electrical circuit means further includes
first latching relay means connected with said first photoelectric cell sensing means for being activated thereby when said first sensing means senses the presence of a fastener tab in the desired position on the one side of the moving material and connected with said relay of said first relay operated switch means for activation thereof when activated by said first photoelectric cell sensing means,
third cam operated timer switch means connected with said first latching relay means for deactivating said latching relay means and thus deactivating said relay of said first relay operated switch means during predetermined timed periods in which the absence of a fastener tab is desired to be sensed by said first photoelectric cell sensing means,
second latching relay means connected with said second photoelectric cell sensing means for being activated thereby when said second photoelectric cell sensing means senses the presence of a fastener tab in the desired position on the other side of the moving material and connected with said relay of said second relay operated switch means for actuation thereof when activated by said second photoelectric cell sensing means, and
fourth cam operated timer switch means connected with said second latching relay means for deactivating said second latching relay means and thus deactivating said relay of said second relay operated switch means during predetermined timed periods in which the absence of a fastener tab is desired to be sensed by said second photoelectric cell sensing means.

12. Apparatus, as set forth in claim 11, in which said electrical circuit means further includes
manually operated normally open start switch means in said circuit for being momentarily closed to initiate the flow of electrical energy to said drive means,
manually operated normally closed stop switch means in said circuit for being opened to stop the flow of electrical energy to said drive means,
relay operated normally open holding switch means connected in said circuit in series with said start switch means and said stop switch means for being closed by said start switch means when said start switch means is momentarily closed for maintaining the flow of electrical energy to said drive means and for being held closed by said stop switch means until said stop switch means is opened,
relay operated stop motion switch means comprising a relay connected in series with said first and second timer operated switch means and said first and second, sensing means responsive, relay operated switch means for being activated and deactivated thereby, and a normally open switch connected in said circuit in series with said relay operated holding switch means for being closed upon activation of said stop motion relay for maintaining said holding switch means closed and for being opened upon deactivation of said stop motion relay for opening said holding switch means to stop the flow of electrical energy to said drive means, and
timer operated reset switch means connected in series in said circuit with said stop motion relay for closing of said normally open stop motion switch after said stop motion switch has been opened to stop the flow of electrical energy to said drive means for allowing restarting by said start switch means.

* * * * *

UNITED STATES PATENT OFFICE
CERTIFICATE OF CORRECTION

PATENT NO. : 4,089,728
DATED : May 16, 1978
INVENTOR(S) : Richard K. Teed

It is certified that error appears in the above-identified patent and that said Letters Patent are hereby corrected as shown below:

Column 1, line 52, "491,739" should be --491,793--
Column 7, line 37, "position" should be --positions--

Signed and Sealed this

Twenty-sixth Day of September 1978

[SEAL]

Attest:

RUTH C. MASON
Attesting Officer

DONALD W. BANNER
Commissioner of Patents and Trademarks